(12) United States Patent
Babcock, IV et al.

(10) Patent No.: US 10,564,127 B2
(45) Date of Patent: Feb. 18, 2020

(54) AUGMENTED REALITY VISUALIZATION FOR PIPE INSPECTION

(71) Applicant: The Charles Stark Draper Laboratory, Inc., Cambridge, MA (US)

(72) Inventors: Philip S. Babcock, IV, Westford, MA (US); Michael Stillo, Somerville, MA (US); Kimberly Ryan, Malden, MA (US); Emily Vincent, Somerville, MA (US); Kelly Sprehn, Waltham, MA (US); Ryan M. Brill, Cambridge, MA (US); Gregory G. Busillo, Belmont, MA (US); Fei Sun, Belmont, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 0 days.

(21) Appl. No.: 15/914,200

(22) Filed: Mar. 7, 2018

(65) Prior Publication Data
US 2018/0259486 A1    Sep. 13, 2018

Related U.S. Application Data

(60) Provisional application No. 62/468,169, filed on Mar. 7, 2017.

(51) Int. Cl.
  *G01N 27/82* (2006.01)
  *G06T 19/00* (2011.01)
  (Continued)

(52) U.S. Cl.
  CPC ........... *G01N 27/82* (2013.01); *G01N 17/006* (2013.01); *G06T 19/006* (2013.01); *H04N 13/344* (2018.05)

(58) Field of Classification Search
  CPC .......... G01N 2291/02863; G01N 27/82–9093; G06T 19/006
  See application file for complete search history.

(56) References Cited

U.S. PATENT DOCUMENTS

| 9,366,653 B2* | 6/2016 | O'Keefe | G01B 17/02 |
| 2010/0159434 A1* | 6/2010 | Lampotang | G09B 9/00 434/365 |

(Continued)

FOREIGN PATENT DOCUMENTS

WO   WO 2015/120550 A1   8/2015

OTHER PUBLICATIONS

Lawson, Shaun W., and John RG Pretlove. "Augmented reality for underground pipe inspection and maintenance." Telemanipulator and Telepresence Technologies V. vol. 3524. International Society for Optics and Photonics, 1998. (Year: 1998).*

(Continued)

*Primary Examiner* — Ryan McCulley
(74) *Attorney, Agent, or Firm* — Sunstein Kann Murphy & Timbers LLP

(57) ABSTRACT

A defect visualization system includes an augmented reality display system to display an image representing a defect, such as missing metal, in a ferromagnetic material when a user gazes at a portion of the ferromagnetic material hosting the defect, based on magnetic field data provide by a magnetometry system, thereby facilitating locating the defect and replacing magnetometers after the defect has been repaired, even if location references originally present on cladding material are lost or destroyed during the repair.

42 Claims, 15 Drawing Sheets

(51) Int. Cl.
   *G01N 17/00*   (2006.01)
   *H04N 13/344*  (2018.01)

(56) References Cited

U.S. PATENT DOCUMENTS

| | | | |
|---|---|---|---|
| 2014/0026667 A1* | 1/2014 | O'Keefe | G01B 17/02 |
| | | | 73/622 |
| 2015/0039245 A1* | 2/2015 | Langlois | G01N 29/043 |
| | | | 702/39 |
| 2015/0317833 A1 | 11/2015 | Ebstyne et al. | |
| 2015/0330946 A1 | 11/2015 | Davis et al. | |
| 2016/0140868 A1* | 5/2016 | Lovett | G09B 19/0053 |
| | | | 434/118 |
| 2016/0239080 A1* | 8/2016 | Marcolina | G06F 3/011 |
| 2016/0249989 A1* | 9/2016 | Devam | A61B 5/024 |
| | | | 345/633 |
| 2017/0046877 A1* | 2/2017 | Hustad | G06F 3/147 |
| 2017/0108469 A1 | 4/2017 | Timmons et al. | |
| 2017/0122909 A1* | 5/2017 | Goroshevskiy | G01N 27/82 |
| 2018/0218538 A1* | 8/2018 | Short | G06T 19/006 |

OTHER PUBLICATIONS

Liu, Zheng, and Yehuda Kleiner. "State of the art review of inspection technologies for condition assessment of water pipes." Measurement 46.1 (2013): 1-15. (Year: 2013).*
Wikipedia, "Augmented reality," https://en.wikipedia.org/w/index.php?title=Augmented_reality&oldid=768944636, 26 pages, Mar. 6, 2017.
International Searching Authority, European Patent Office, International Search Report and Written Opinion, International Application No. PCT/US2018/021287, 14 pages, dated May 22, 2018.

* cited by examiner

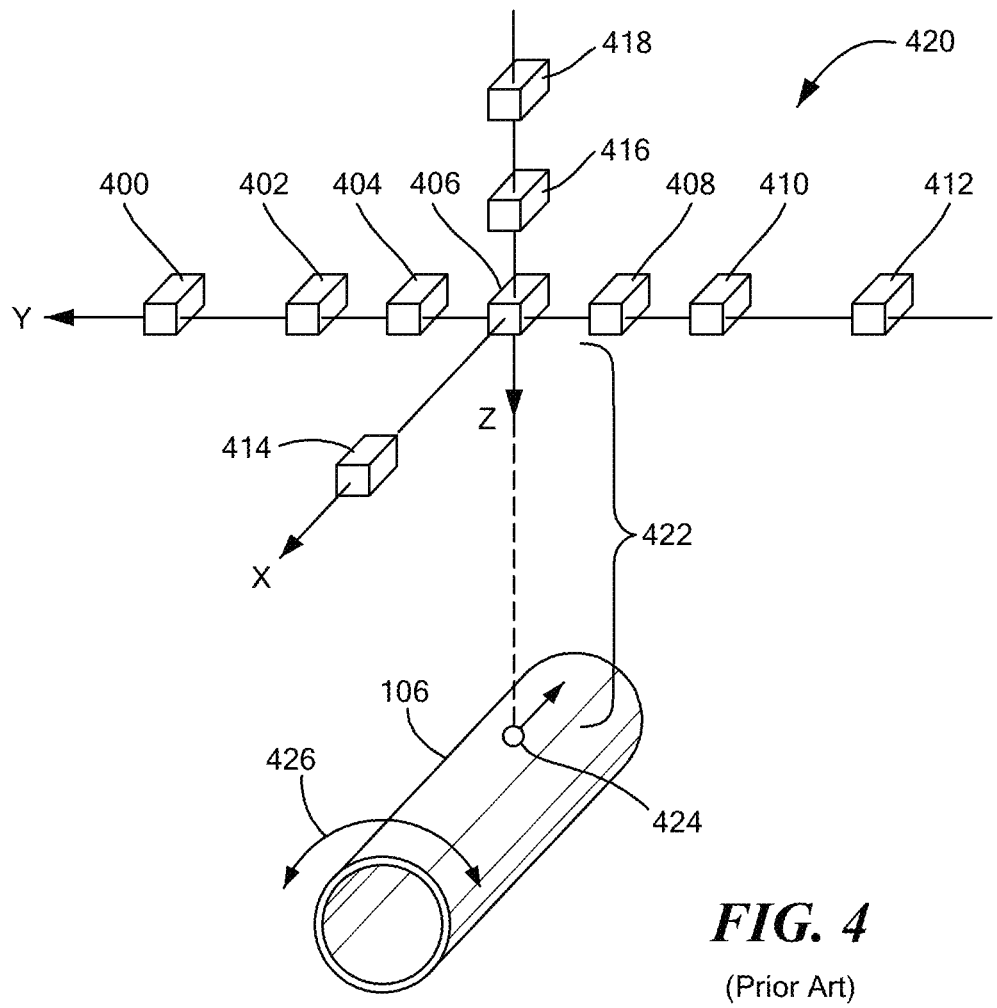
FIG. 4
(Prior Art)
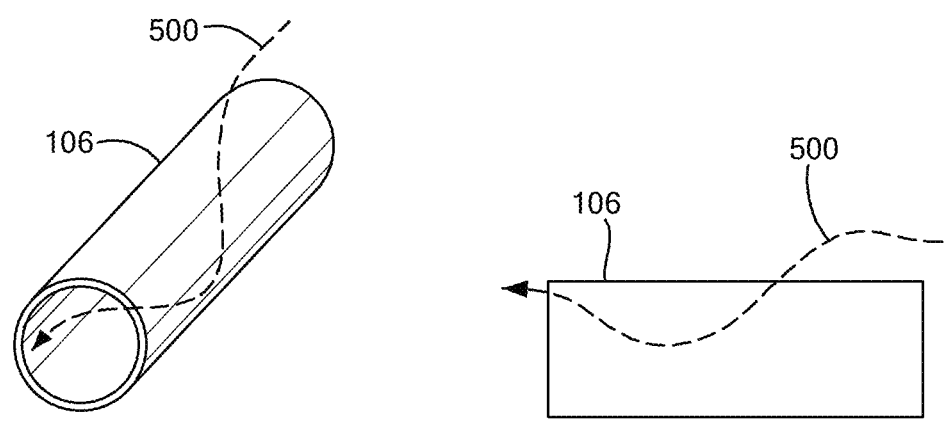
FIG. 5          FIG. 6

AUGMENTED REALITY VISUALIZATION FOR PIPE INSPECTION

CROSS REFERENCE TO RELATED APPLICATIONS

This application claims the benefit of U.S. Prov. Pat. Appl. No. 62/468,169, filed Mar. 7, 2017, titled "Augmented Reality Visualization for Pipe Inspection," the entire contents of which are hereby incorporated by reference herein, for all purposes.

BACKGROUND

Technical Field

The present invention relates to detecting defects in ferromagnetic materials and, more particularly, to systems that facilitate visualizing detected defects.

Related Art

Ferromagnetic materials, such as iron, nickel, steel and other materials, are used to make many items, such as pipes, beams and ocean vessel hulls. Defects, which may develop in the ferromagnetic materials over time, can cause problems. Prior art systems can provide location information about a defect. However, actually locating a physical portion of a ferromagnetic material, such as a buried pipe, to gain physical access to the portion that contains the defect remains very difficult.

As used herein, "ferromagnetic material" includes both ferromagnetic and ferrimagnetic material. In many cases, these materials are subject to corrosion and/or erosion. As used herein, corrosion means loss of material as a result of chemical reaction, most commonly oxidation. As used herein, erosion means loss of material as a result of a mechanical process, such as abrasion. For example, sand produced in an oil or gas well can abrade the inside of a pipeline carrying oil or gas from the well. Material loss due to corrosion and/or erosion is collectively referred to herein as a "defect." As used herein, the term defect also includes a crack, or a void or inclusion of foreign material, such as might occur during manufacture or later. If allowed to occur beyond a critical point, corrosion, erosion or another defect may compromise structural integrity of an item, possibly resulting in a catastrophic failure, such as an oil spill, building collapse or ship sinking.

Magnetometry-based systems and method for detecting defects in ferromagnetic material are known, as exemplified in U.S. Pat. No. 9,651,471 ('471), issued May 16, 2017, titled "System and Method of Measuring Defects in Ferromagnetic Materials," U.S. Pat. No. 9,651,472 ('472), issued May 16, 2017, titled "System and Method of Measuring Defects in Ferromagnetic Materials," U.S. patent application Ser. No. 15/197,699 ('699), filed Jun. 29, 2016, titled "System and Method for Characterizing Ferromagnetic Material," and U.S. patent application Ser. No. 15/653,036 ('036), filed Jul. 18, 2017, titled "System and Method for Characterizing Ferromagnetic Material," the entire contents of each of which are hereby incorporated by reference herein, for all purposes.

However, pipe inspection, repair and/or replacement, particularly in a large, complex facility, such as a processing plant, requires an ability to locate both a detection device and a defect the detection device finds. Geolocation, i.e., stating where in the facility the device or defect is, has been historically done by using sector and pipe identifiers from drawings of the facility. While useful when looking at data in a control center, this information is cumbersome in the actual facility, where many of these reference location identifiers are not present. Furthermore, in some situations, precise location of the defect is a critical piece of knowledge in both diagnosing the defect and selecting next steps to be performed.

When a magnetometry-based detector is used, an output of the detector gives indications of the defect location, but locating this position directly on the pipe can be difficult. In the case of a scanning magnetometry system, one needs to recreate the scan locations to find the precise location of the defect. For permanently-mounted magnetometry systems, the defect is below the sensor area and, therefore, difficult to precisely locate, if the magnetometry sensor is removed, which is typically done for further analysis, inspection or repair of the defect.

Often, industrial pipes are coated with protective layers and/or layers of insulation with cladding over the insulation. It is very difficult to translate any location points that may be marked on the insulation, or its cladding, down to the pipe itself, because removing the cladding, insulation and pipe coatings destroys the reference points. Since pipe defects tend to be internal to the pipe, there is no external visual clue as to the defect location, even when all of the pipe coverings have been removed.

Thus, although prior art systems can provide location information about a defect, actually locating a physical portion of a ferromagnetic material, such as a buried pipe, to gain physical access to the portion that contains the defect remains very difficult.

SUMMARY OF EMBODIMENTS

An embodiment of the present invention provides a system for visualizing defects in ferromagnetic material. The system includes a source of magnetic field data. The magnetic field data characterizes location of the defect on or in the ferromagnetic material. The system also includes a display device. The display device is configured to generate an image perceivable by a human. The system also includes an augmented reality system. The augmented reality system is coupled to receive the magnetic field data. The augmented reality system causes display, by the display device, of an image. The image represents the magnetic field data, such that the image registers, as viewed by the human, with the ferromagnetic material.

The magnetic field data may characterize location of metal missing from the ferromagnetic material.

The display device may include a head-worn mounted display, such as a stereoscopic vision display device.

The display device may include a 3D projector, such as a holographic projector.

The display device may include a hand-held device that includes a display screen. The display screen may include a stereoscopic vision display screen.

The display device may further include a camera, and the display device may be configured to display an image captured by the camera, overlaid with the image representing the magnetic field data.

The image representing the magnetic field data may include first icons. The first icons may represent magnetometers that detected a magnetic field proximate the ferromagnetic material and from which the magnetic field data was derived. The first icons may register, as viewed by the human, with the ferromagnetic material.

The image representing the magnetic field data may include a second icon. The second icon may be visually distinct from the first icons. The second icon may represent a failed magnetometer.

The image representing the magnetic field data may include historical information about the magnetic field data. The historical information may register, as viewed by the human, with the ferromagnetic material.

The historical information may include a graph showing estimated thickness of the ferromagnetic material over time.

The image representing the magnetic field data may include a graph. The graph may represent relative strength of a magnetic field proximate the ferromagnetic material and from which the magnetic field data was derived. The graph may register, as viewed by the human, with the ferromagnetic material.

The image representing the magnetic field data may include a graphical representation of the defect on or in the ferromagnetic material. The graphical representation may register, as viewed by the human, with the ferromagnetic material.

The image representing the magnetic field data may include a defect depth map, such that the defect depth map registers, as viewed by the human, with the ferromagnetic material.

The image representing the magnetic field data may include one or more of: a fault code, battery charge level information, a system serial number, sensor array identification information, system diagnostic information, geolocation information about the magnetic field data represented in the image and/or a failed sensor indicator.

The source of magnetic field data may include a plurality of magnetometers. The plurality of magnetometers may be disposed proximate a surface of the ferromagnetic material. Each magnetometer of the plurality of magnetometers may be fixed in position, relative to the ferromagnetic material.

The source of magnetic field data may include a plurality of magnetometers arranged in an array. The array may be positionable at a standoff distance from the ferromagnetic material. The array may be translatable along an axis to a plurality of scan positions along the ferromagnetic material.

The image representing the magnetic field data may include an indication of a path taken by the array. The indication of the path may register, as viewed by the human, with the ferromagnetic material.

Another embodiment of the present invention provides a method for visualizing defects in ferromagnetic material. The method includes generating magnetic field data. The magnetic field data characterizes location of from the defect on or in the ferromagnetic material. A display device is provided. The display device is configured to generate an image perceivable by a human. An augmented reality system is provided. The augmented reality system is coupled to receive the magnetic field data. An image representing the magnetic field data is displayed by the display device. The image is displayed, such that the image registers, as viewed by the human, with the ferromagnetic material.

The magnetic field data may characterize location of metal missing from the ferromagnetic material.

Providing the display device may include providing a head-mounted display, such as a stereoscopic vision display device.

Providing the display device may include providing a 3D projector, such as a holographic projector.

Providing the display device may include providing a hand-held device that includes a display screen, such as a stereoscopic vision display screen.

A camera may be provided. An image captured by the camera may be displayed by the display device. The image captured by the camera may be overlaid with the image representing the magnetic field data.

Displaying the image representing the magnetic field data may include displaying first icons, The first icons may represent magnetometers that detected a magnetic field proximate the ferromagnetic material and from which the magnetic field data was derived The image may be displayed, such that the first icons register, as viewed by the human, with the ferromagnetic material.

Displaying the image representing the magnetic field data may include displaying a second icon. The second icon may be visually distinct from the first icons. The second icon may represent a failed magnetometer.

Displaying the image representing the magnetic field data may include displaying historical information about the magnetic field data. The historical information may register, as viewed by the human, with the ferromagnetic material.

Displaying the historical information may include estimating thickness of the ferromagnetic material over time and displaying a graph showing the estimated thickness of the ferromagnetic material over time.

Displaying the image representing the magnetic field data may include displaying a graph. The graph may represent relative strength of a magnetic field proximate the ferromagnetic material and from which the magnetic field data was derived. The image may be displayed, such that the graph registers, as viewed by the human, with the ferromagnetic material.

Displaying the image representing the magnetic field data may include displaying a graphical representation of the defect on or in the ferromagnetic material. The image may be displayed, such that the graphical representation registers, as viewed by the human, with the ferromagnetic material.

Displaying the image representing the magnetic field data may include displaying a defect depth map, such that the defect depth map registers, as viewed by the human, with the ferromagnetic material.

Displaying the image representing the magnetic field data may include displaying one or more of: a fault code, battery charge level information, a system serial number, sensor array identification information, system diagnostic information, geolocation information about the magnetic field data represented in the image and/or a failed sensor indicator.

Generating the magnetic field data may include providing a plurality of magnetometers. The plurality of magnetometers may be disposed proximate a surface of the ferromagnetic material. Each magnetometer of the plurality of magnetometers may be fixed in position, relative to the ferromagnetic material.

Generating the magnetic field data may include providing a plurality of magnetometers arranged in an array. The array may be positioned at a standoff distance from the ferromagnetic material. The array may be translated along an axis to a plurality of scan positions along the ferromagnetic material.

Displaying the image representing the magnetic field data may include displaying an indication of a path taken by the array. The indication of the path may be displayed, such that the indication of the path registers, as viewed by the human, with the ferromagnetic material.

Yet another embodiment of the present invention provides a computer program product for visualizing defects in ferromagnetic material. The computer program product includes a non-transitory computer-readable medium. Computer readable program code is stored on the non-transitory computer-readable medium. When executed by a processor, the program code establishes processes. The processes a process that generates magnetic field data. The magnetic field data characterizes location of the defect on or in the ferromagnetic material. A process drives a display device. The display device is configured to generate an image perceivable by a human. An augmented reality process is coupled to receive the magnetic field data. The augmented reality process causes display, by the display device, of an image. The image represents the magnetic field data. The image is displayed, such that the image registers, as viewed by the human, with the ferromagnetic material.

The magnetic field data may characterize location of metal missing from the ferromagnetic material.

BRIEF DESCRIPTION OF THE DRAWINGS

The invention will be more fully understood by referring to the following Detailed Description of Specific Embodiments in conjunction with the Drawings, of which:

FIG. 4 is a schematic illustration of an array of magnetometers for scanning the pipe of FIGS. 1 and 2, according to the prior art.

FIGS. 5 and 6 are respective isometric and side views of the pipe of FIG. 1-4 showing a hypothetical path taken by the array of magnetometers.

DETAILED DESCRIPTION OF SPECIFIC EMBODIMENTS

Embodiments of the present invention enable a field operator to visualize, as a humanly-visible image, magnetic or other analytical data obtained by a scanning or permanently mounted magnetometry system on a real pipe or other ferromagnetic material, and to follow the image down, layer by layer, as various coverings are removed. These embodiments facilitate precise comparative diagnosis via other inspection tools, such as tools that require direct pipe contact. This collaboration between magnetometry sensing and other sensing modes enables quick and precise location, diagnosis and repair of ferromagnetic materials. Furthermore, after a diagnostic or repair operation has been performed, these embodiments facilitate precise reinstallation of removed sensors to the same locations from which the sensors were removed.

Figure 1:
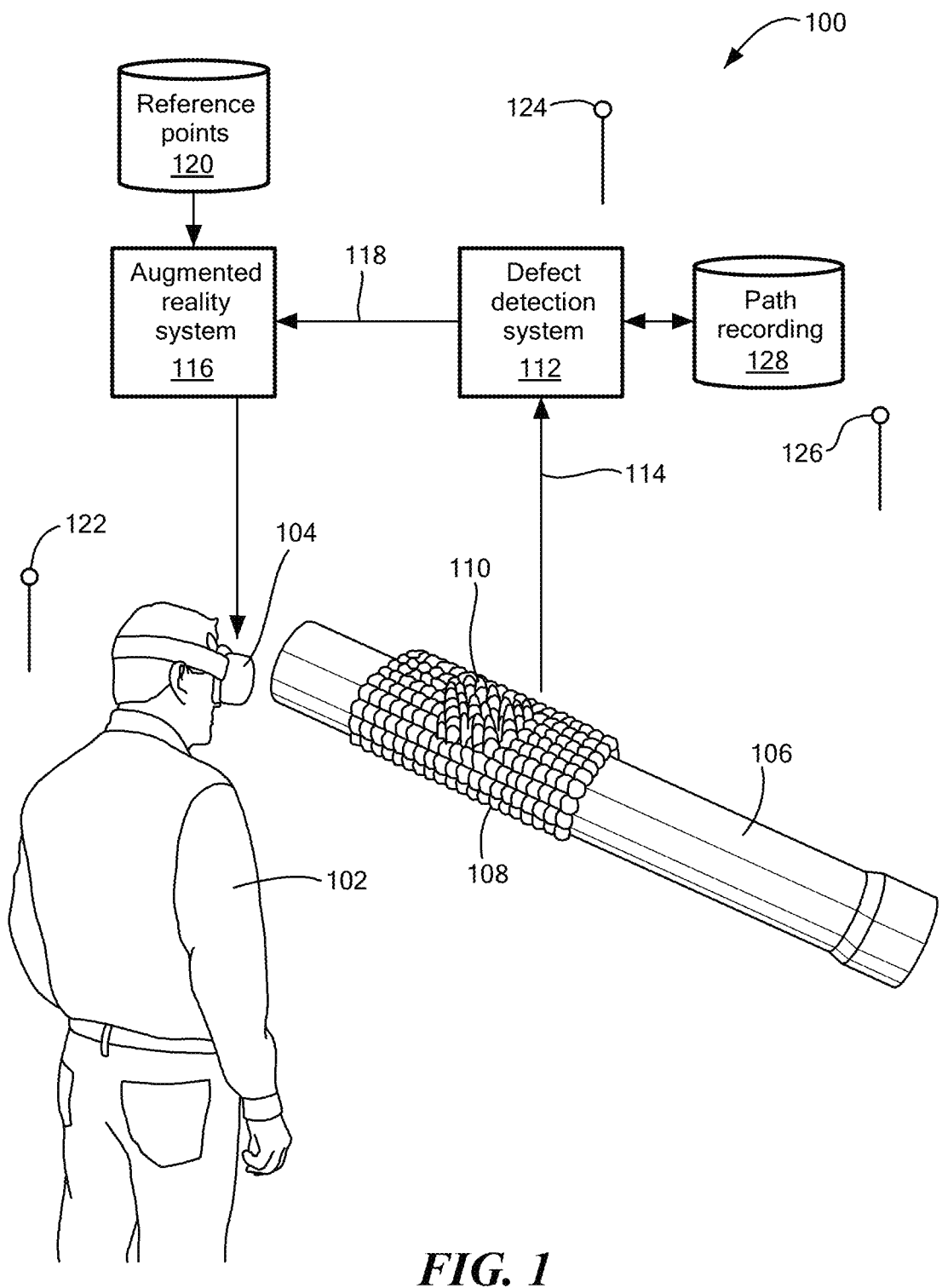
FIG. 1 is a schematic diagram of a system for visualizing defects in ferromagnetic material, according to an embodiment of the present invention, including an illustration of a hypothetical augmented reality scene, as augmented by the system to display a color-coded, three-dimensional defect depth map along a ferromagnetic material (a pipe).

FIG. 1 is a schematic diagram of a system 100 for visualizing defects in ferromagnetic material, according to an embodiment of the present invention. FIG. 1 includes an illustration of a hypothetical augmented reality scene, as augmented by the system 100. A human user 102 using a suitable display device 104, such as a HoloLens augmented reality visualization (ARV) display from Microsoft Corporation, One Microsoft Way, Redmond, Wash. 98052-6399, sees a real ferromagnetic pipe 106 and perceives an image 108 representative of magnetic field data.

In this embodiment, the magnetic field data are represented in the image 108 by a color-coded, three-dimensional defect depth map 110. The image 108 with the defect depth map 110 is generated by the ARV display device 104, such that the defect depth map 110 appears to the user 102 to be registered with the pipe 106. Thus, if the user 102 changes gaze direction or tilt, or the user 102 moves to another location, the image 108 is automatically correspondingly changed.

The defect depth map 110 includes a surface corresponding to each location at which a measurement has been made or calculated. Height of the surface above a nominal height indicates a depth at which a corresponding defect has been detected. The surfaces may be color-coded to indicate severity of the defect, such as by coloring surfaces that represent no defect green, moderate defect yellow and severe defect red.

Figure 2:
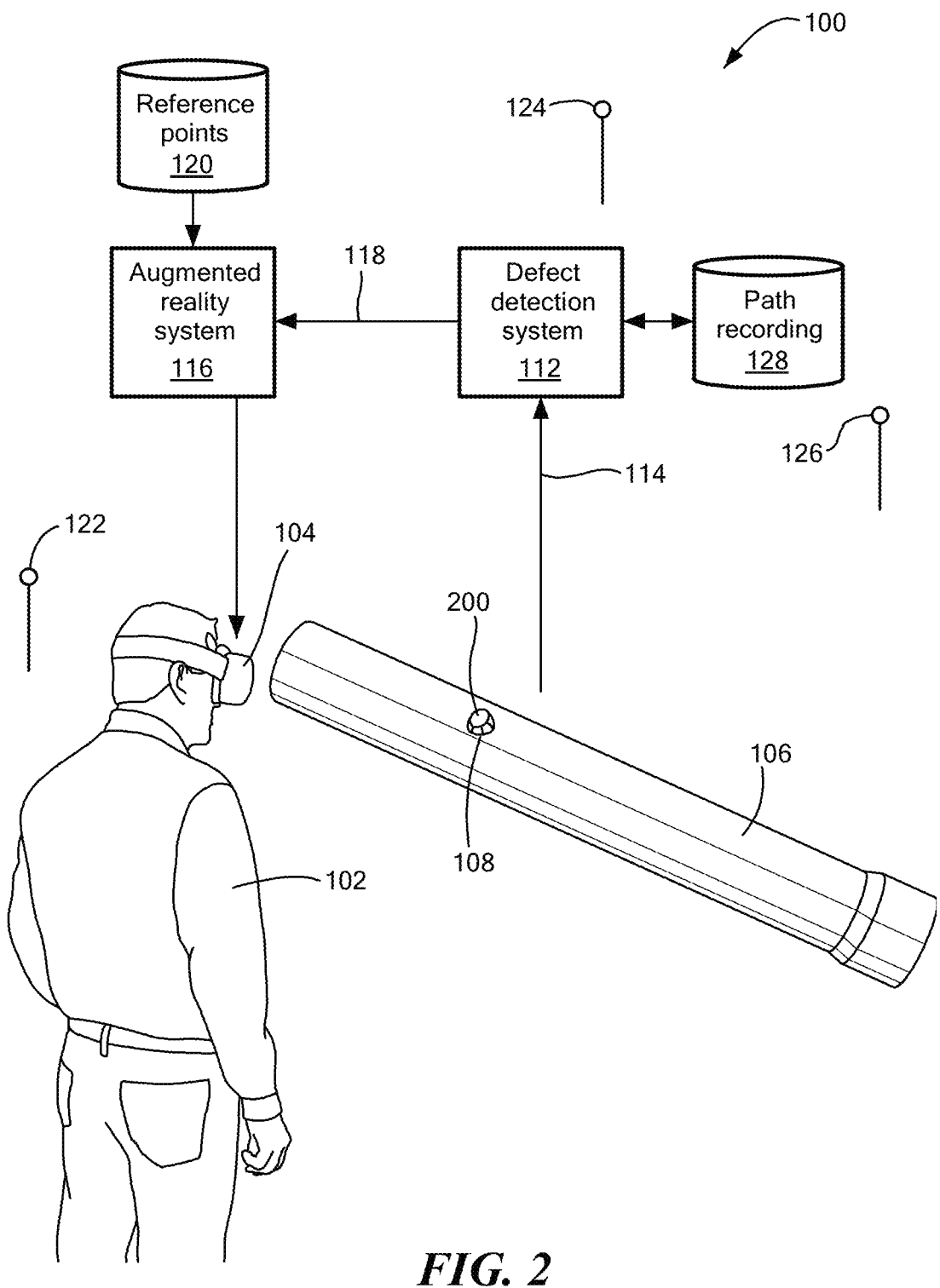
FIG. 2 is a schematic diagram of the system of FIG. 1, including an illustration of a hypothetical augmented reality scene, as augmented by the system to a display a graphical image of, or an icon representing, missing metal or defect, according to another embodiment of the present invention.

In other embodiments, the magnetic field data may be represented differently, such as by a computer generated graphical image 200 of, or an icon representing, missing metal or a defect, as shown in FIG. 2. As in the embodiment described with respect to FIG. 1, the graphical image 200 or icon is generated by the ARV display device 104, such that the graphical image 200 or icon appears to the user 102 to be registered with the pipe 106.

Figure 3:
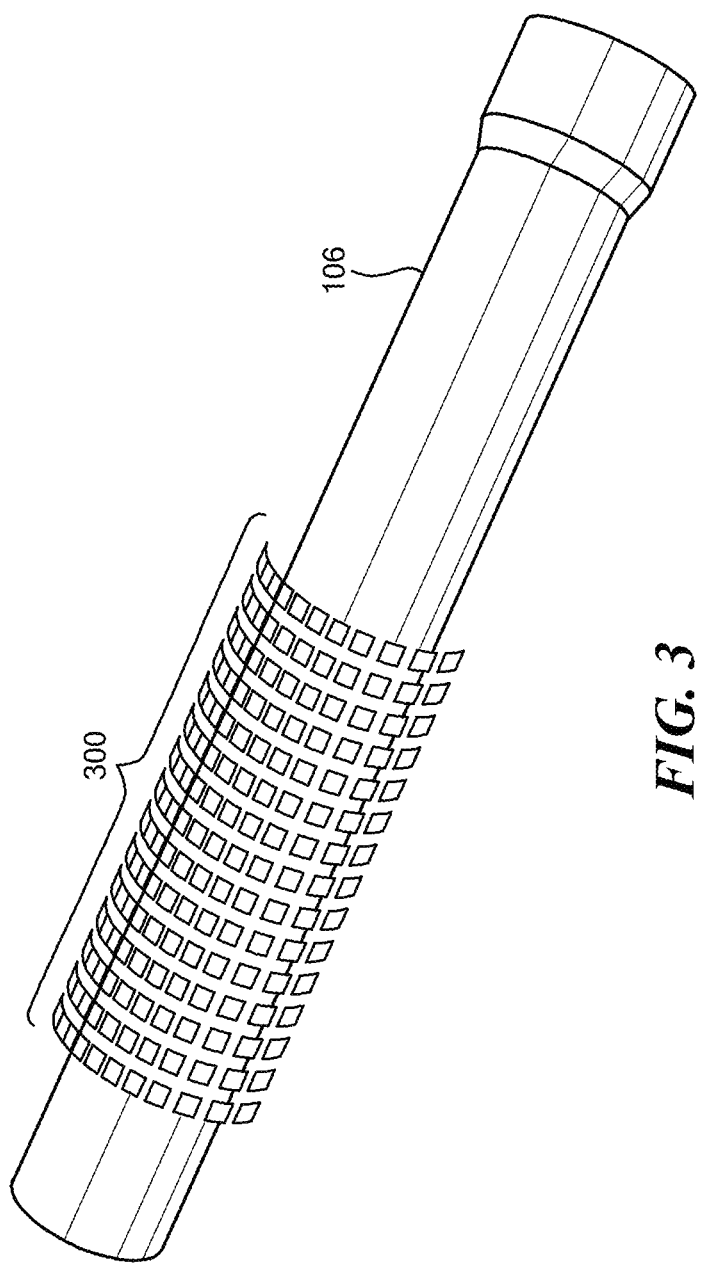
FIG. 3 illustrates an exemplary arrangement of magnetometers proximate the pipe of FIGS. 1 and 2, according to the prior art.

Returning to FIG. 1, the magnetic field data characterizes locations of the defect, such as metal missing from the pipe 106. The location of the defect is determined by a defect detection system 112 that receives signals 114 from magnetometers (not visible) proximate the pipe 106. FIG. 3 illustrates an exemplary arrangement of the magnetometers 300 proximate the pipe 106. The magnetometers 300 may be arranged in arrays ("patches"), such as arrays of 16×16 magnetometers, and the patches may be spaced apart longitudinally and/or circumferentially along and/or around the pipe 106. The magnetometers of a given patch may, but need not, extend all the way around the pipe 106. The '471 and '472 patents describe suitable fixed-in-place magnetometry systems.

The magnetometers need not, however, be fixed in place, relative to the pipe 106. For example, as shown schematically in FIG. 4, one or more magnetometers, exemplified by magnetometers 400-418, may be arranged in an array 420. The array 420 may be positionable at a standoff distance 422 along a z axis from the ferromagnetic material 106, and translatable along an x axis, to a plurality of scan positions along the ferromagnetic material 106. The array 420 may be a one-, two- or three-dimensional array. The x axis may be perpendicular to the z axis. Thus, the array 420 of magnetometers 400-418 may be scanned above the pipe 106 to detect a defect 424, as described in the '699 and '036 applications.

It may or may not be possible to maintain a relatively constant standoff distance 422 while scanning along the pipe 106, and it may not be practical to scan the array 420 along a straight line, for example as a result of rugged terrain through which the pipe extends and jostling of a vehicle, or stride of a human, transporting the array 420. For example, as the array 420 scans generally along the length of the pipe 106, the standoff distance 422 may vary, and the "clock angle" 426 of the array 420 (i.e., position of the array 420 around the pipe 106, as seen in a cross-sectional view of the pipe 106) may vary. For example, the array 420 may follow a non-straight path 500, as shown in isometric view in FIG. 5 and in side view in FIG. 6.

Returning again to FIG. 1, an augmented reality system 116 receives the magnetic field data 118 from the defect detection system 112 and causes the display device 104 to display the image 108 containing the defect depth map 110 or other indicator. The augmented reality system 116 may be initialized with data 120 about reference points in areas of a facility where the inspection system 100 is expected to be used. For example, fiducials, exemplified by fiducials 122, 124 and 126, in the facility may be used to initialize the augmented reality system 116, as known in the art. In this case, the data 120 may contain information about the fiducials 122-126. Alternatively, other known initialization techniques may be used, such as those involving global position system (GPS) receivers, star trackers, inertial navigation systems (INSs), etc. In this way, fixed, known reference points may be registered in the system 100, and these reference points may serve to place various magnetometry systems, with respect to the plant, specific pipes and locations on those pipes.

Figure 7:
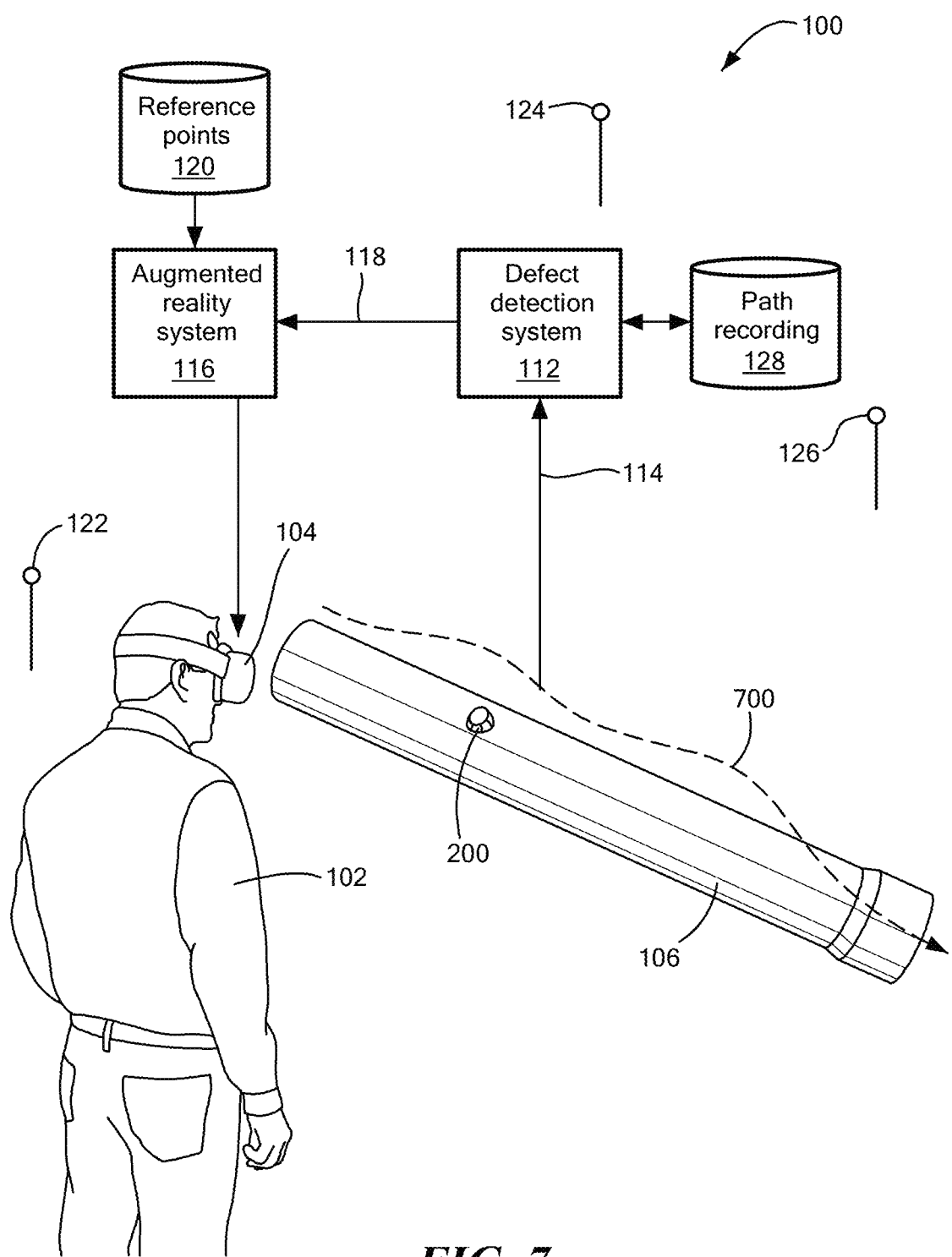
FIG. 7 is a schematic diagram of the system of FIG. 1, including an illustration of a hypothetical augmented reality scene, as augmented by the system to display a representation of the path of FIGS. 5 and 6 taken by the array of magnetometers of FIG. 4, according to another embodiment of the present invention.

For a scanning magnetometry system, such as the system discussed with respect to FIGS. 4-6, the scan itself can be recorded by the system 100, such as by the defect detection system 112, for example in a path recording database 128 (FIG. 1), and this recording 128 may serve to place the resulting data into a reference frame, relative to the pipe 106. This allows virtual imaging of the detected magnetic fields and processed information directly onto the real pipe 106, which guides next steps of a more detailed investigation or repair of the pipe. In addition, this imaging by the system 100 provides a detailed "odometer" function that not only captures motion of the magnetometer array 420 along the pipe 106, but also traces clock angles that the scanner's path 500 traces out, and any other anomalous motions, which can later be removed via correction algorithms. FIG. 7 includes an illustration of the hypothetical augmented reality scene of FIG. 1, as augmented by the system 100 to show an indication 700 of the path 500 (FIGS. 5-6) taken by the array 420, such that the indication 700 of the path 500 registers, as viewed by the human 102, with the ferromagnetic material (pipe 106). Although only one path 500 is indicated in FIG. 7, if the array 420 made multiple scans along the pipe 106, each of these scans may be indicated by a separate line in the augmented image, for example to facilitate correlating the multiple scans to verify effectiveness of a motion compensation algorithm used by the defect detection system 112.

Figure 8:
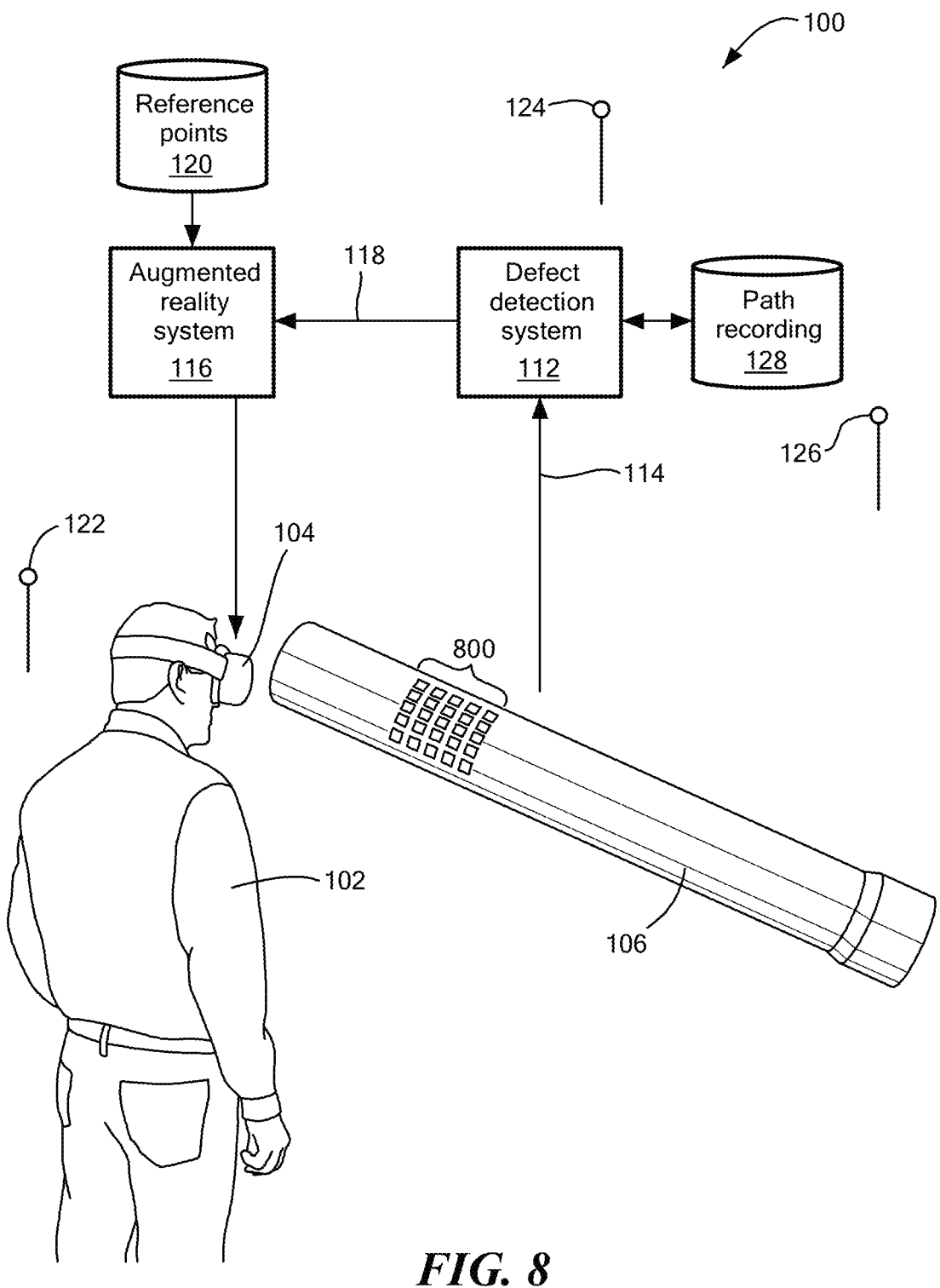
FIG. 8 is a schematic diagram of the system of FIG. 1, including an illustration of a hypothetical augmented reality scene, as augmented by the system to display a graphical image or icon of magnetometer patches on the pipe, according to another embodiment of the present invention.

For a more permanently mounted magnetometry system, such as discussed with respect to FIG. 3, the ARV images 108 may be used to quickly locate the magnetometer patches in the field by superposing a computer-generated graphical image or icon 800 of the magnetometer patches on the pipe 106, as though the pipe 106 were transparent, as shown in FIG. 8. This facilitates locating magnetometers that are located on the far side of the pipe 106 from the user 102 and, therefore, not otherwise visible to the user 102. This also facilitates locating and excavating magnetometers and pipes that are buried in the ground, because the system 100 can treat the ground as transparent to enable the user 102 to visualize the magnetometers while they are still buried. Optionally or alternatively, the augmented reality system 116 may display a computer-generated graphical image or icon to represent the pipe 106 while it is still buried.

The system 100 stores information about the locations of the magnetometers, so the graphical image or icon 800 of the magnetometer patch may be displayed, as shown in FIG. 8, even if the magnetometers are removed from the pipe 106, such as may be necessary to access the surface of the pipe 106 to perform a further diagnostic step or a repair step. For example, once a defect has been identified by the defect detection system 112, the user 102 may wish to perform a further diagnostic test with a surface-contact ultrasonic tester. Removal of the magnetometer patch is typically necessary to enable the ultrasonic tester to contact the surface of the pipe 106. After the further diagnostic test or repair has been completed, the magnetometer patch should be replaced in the same place from which it was removed, to ensure comparability of subsequent measurements to previous measurements. The display of the graphical image or icon 800 of the magnetometer patch, in its previous location, facilitates replacing the magnetometers in their proper positions.

Figure 9:
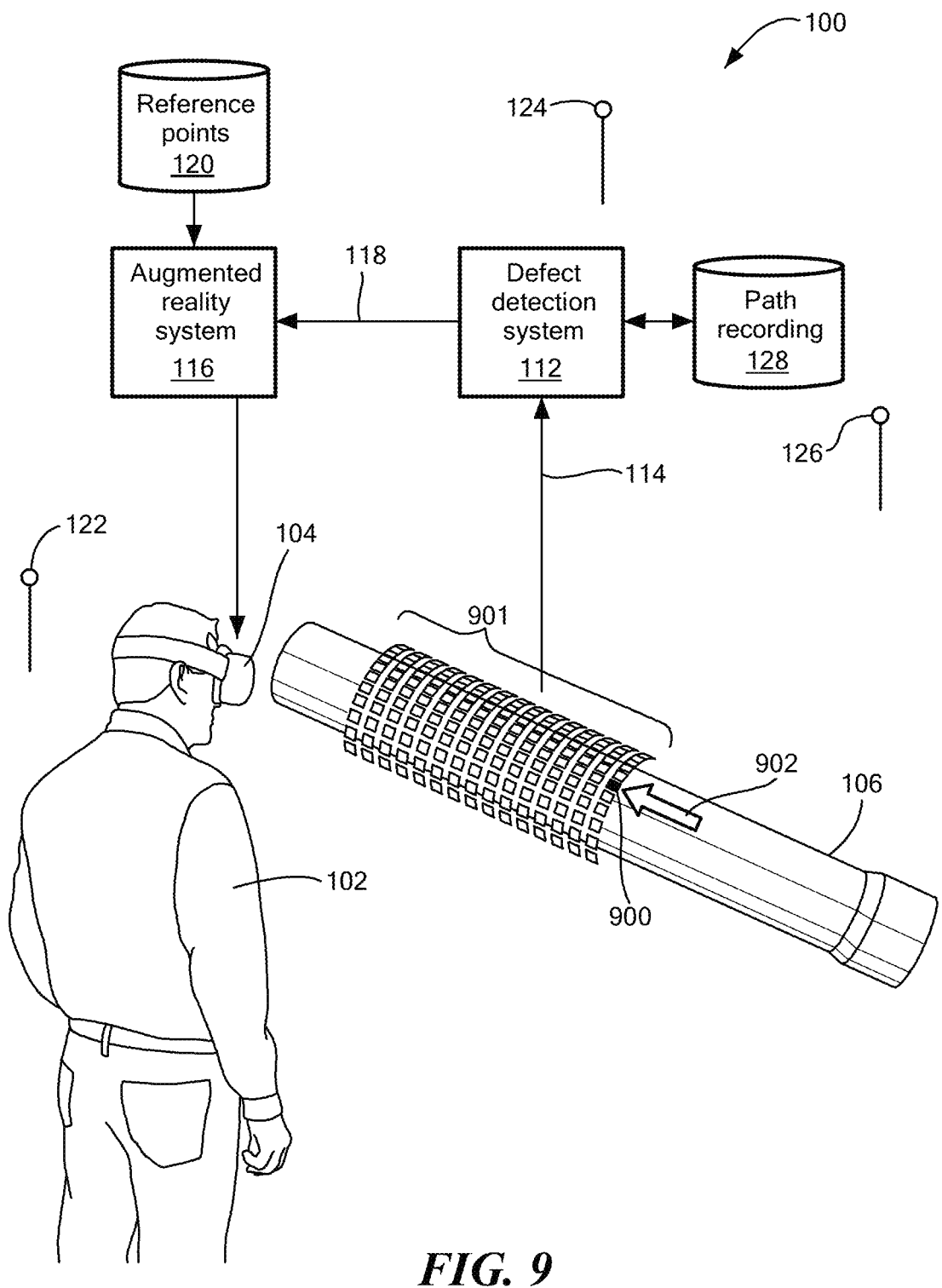
FIG. 9 is a schematic diagram of the system of FIG. 1, including an illustration of a hypothetical augmented reality scene, as augmented by the system to display diagnostic information, including an icon representing a failed magnetometer, according to another embodiment of the present invention.

The system 100 may display system diagnostic information, such as an indication of a failed magnetometer, as shown in FIG. 9. For example, the icon 900 for the failed magnetometer may be displayed in a different color from the other magnetometer icons 901. Optionally, an additional icon, such as an arrow 902, may be displayed to call the user's attention to the icon 900 of the failed magnetometer. Optionally, other information, such as a magnetometer patch identification number, installation date, manufacturer, etc., (not shown) may be displayed as text by the augmented reality system 116 in the display device 104. Similarly, the system 100 may display system diagnostic information about fault codes, battery charge level, energy harvester performance or about another subsystem, such as a wireless computer network used to communicably link the magnetometers together or to a central system.

As discussed with respect to FIG. 1, the display device 104 may include a head-mounted display, such as the aforementioned HoloLens augmented reality visualization display. The display device 104 may generate a monoscopic image (i.e., one image, or identical images for both eyes) for the user 102. However, a display device 104 that generates a stereoscopic image (i.e., a different image for each eye) is preferred.

Alternative Display Devices

As used herein, head-mounted display means a display device that is configured to be supported by a human head and stimulate eyes of the head. Examples include the aforementioned HoloLens ARV display, as well as Google Glass optical head-mounted display, Moverio BT-200 wearable display from Epson and smart contact lenses described by Samsung in Korean Patent Document No. 10-2016-0037008, titled "Smart contact lens for augmented reality and its manufacturing and operation method," the entire contents of which are hereby incorporated by reference herein, for all purposes.

Augmented reality visualization display devices typically enable a user to directly visually perceive the real world, such as through a transparent screen, and overlay graphical images over the user's view of the real world. Instead of such a display device, the display device 104 (FIG. 1) may include a virtual reality display device, which blocks the user's direct view of the real world. In such an embodiment, the virtual reality display device may include a camera to image the real world, and the virtual reality display device may display the image of the real world overlaid with the augmented reality image 108. Suitable virtual reality display devices include Rift virtual reality system, available from Oculus VR, LLC, augmented as needed with a digital camera.

Figure 10:
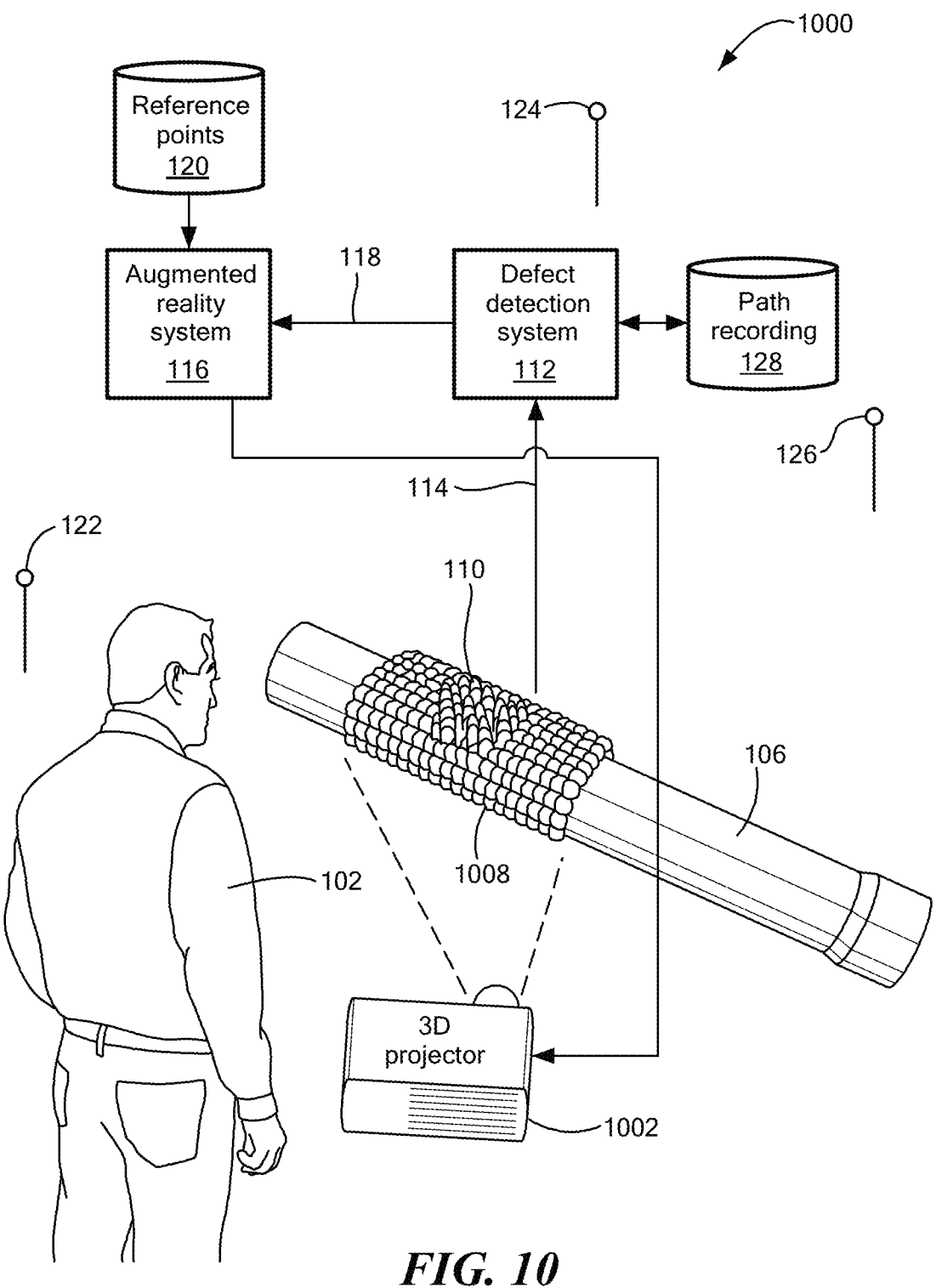
FIG. 10 is a schematic diagram of a system similar to the system of FIG. 1, but here including a 3D projector in place of a head-mounted display device, according to an embodiment of the present invention.

Rather than a head-mounted display device 104, as discussed with respect to FIG. 1, some embodiments, exemplified by a system 1000 shown in FIG. 10, include a 3D projector 1002. The 3D projector 1002 may be, for example, a holographic projector, or any suitable projector capable of projecting an image 1008 that is perceivable by the human 102 as a 3D image. Some suitable 3D projectors require the user 102 to wear special glasses to be able to perceive the 3D image.

Figure 11:
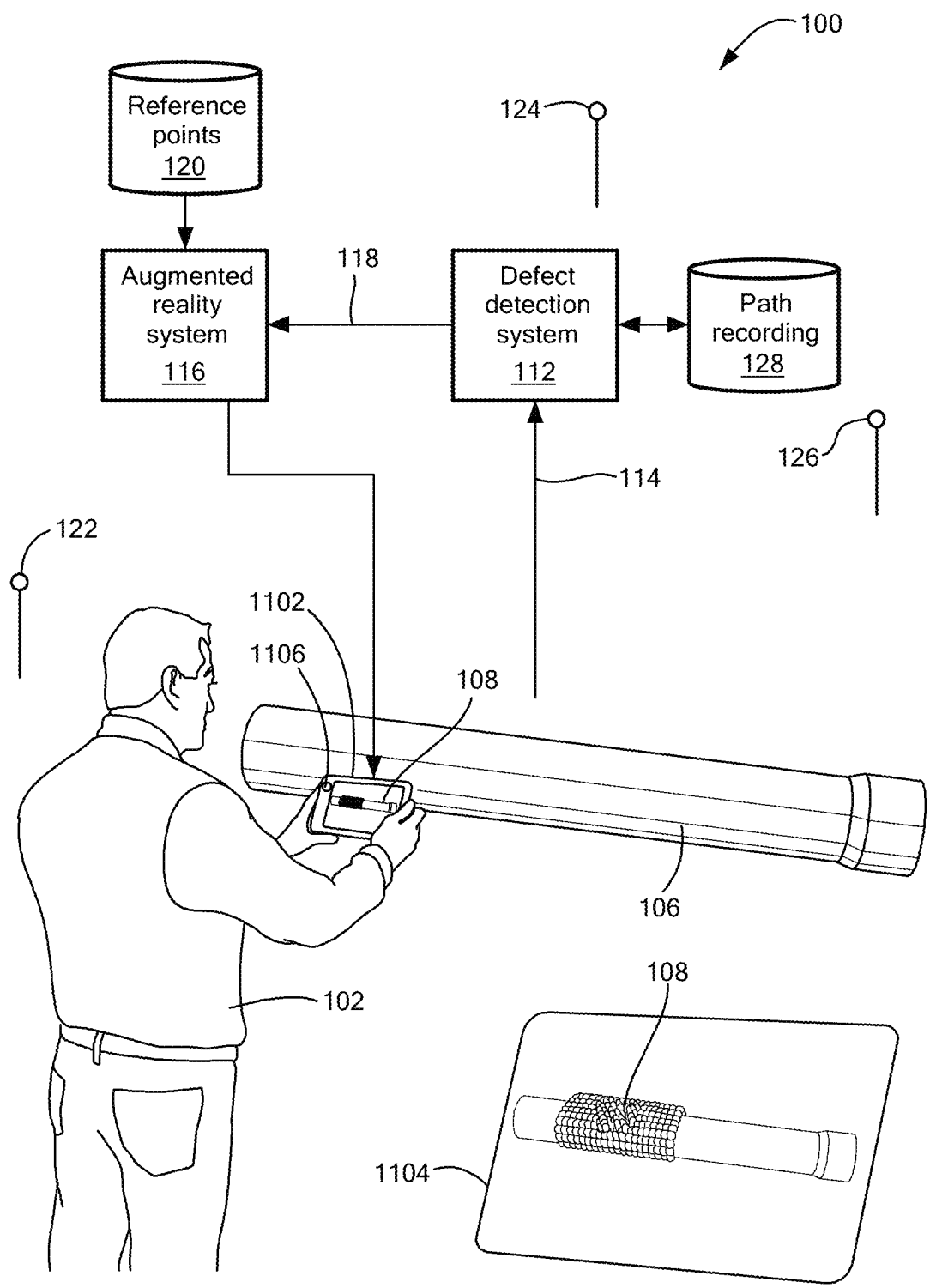
FIG. 11 is a schematic diagram of a system similar to the system of FIG. 1, but here including a hand-held tablet or mobile phone with a display screen in place of a head-mounted display device, according to an embodiment of the present invention.

In yet some other embodiments, exemplified by a system 1100 shown in FIG. 11, a hand-held device 1102, such as a tablet computer or mobile phone with a display screen, may be used as the display device. The display screen of the hand-held device 1102 is shown enlarged at 1104. In FIG. 11, the pipe 106 is assumed to be covered by cladding, hence the magnetometers are not directly visible to the user 102. The hand-held device 1102 may include a camera 1106 on the back of the hand-held device 1102, hence not visible in FIG. 11, and the display device may be configured to display an image captured by the camera, overlaid with the image 108 representing the magnetic field data.

Figure 12:
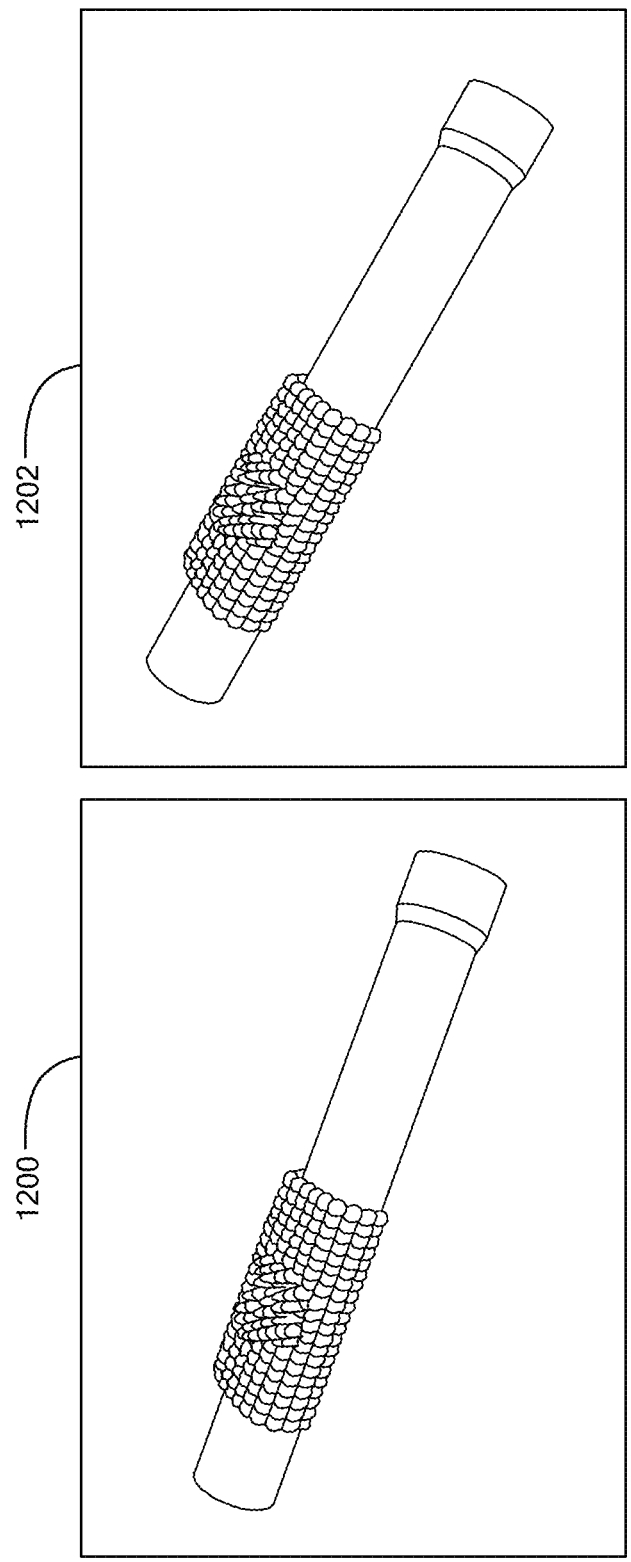
FIG. 12 shows an exemplary pair of views (left and right) that would be collectively perceived by a human as a 3D image, according to an embodiment of the present invention.

A stereoscopic display device can cause the human user 102 to perceive a 3D image by presenting slightly different views of an object to the human's two eyes, as well known. FIG. 12 shows an exemplary pair of views 1200 (left) and 1202 (right) that would be collectively perceived by a human as a 3D image. The hand-held device 1102 (FIG. 11) may generate a 3D image by splitting the screen left-and-right into two subscreens, with the user 102 simultaneously viewing each subscreen with a respective eye. An appropriate holder for the hand-held device 1102, such as Pine smartphone case available from Cordon Development Labs, Toronto, Canada, facilitates such an operation, effectively turning the hand-held device 1102 into a stereoscopic vision display screen.

Figure 13:
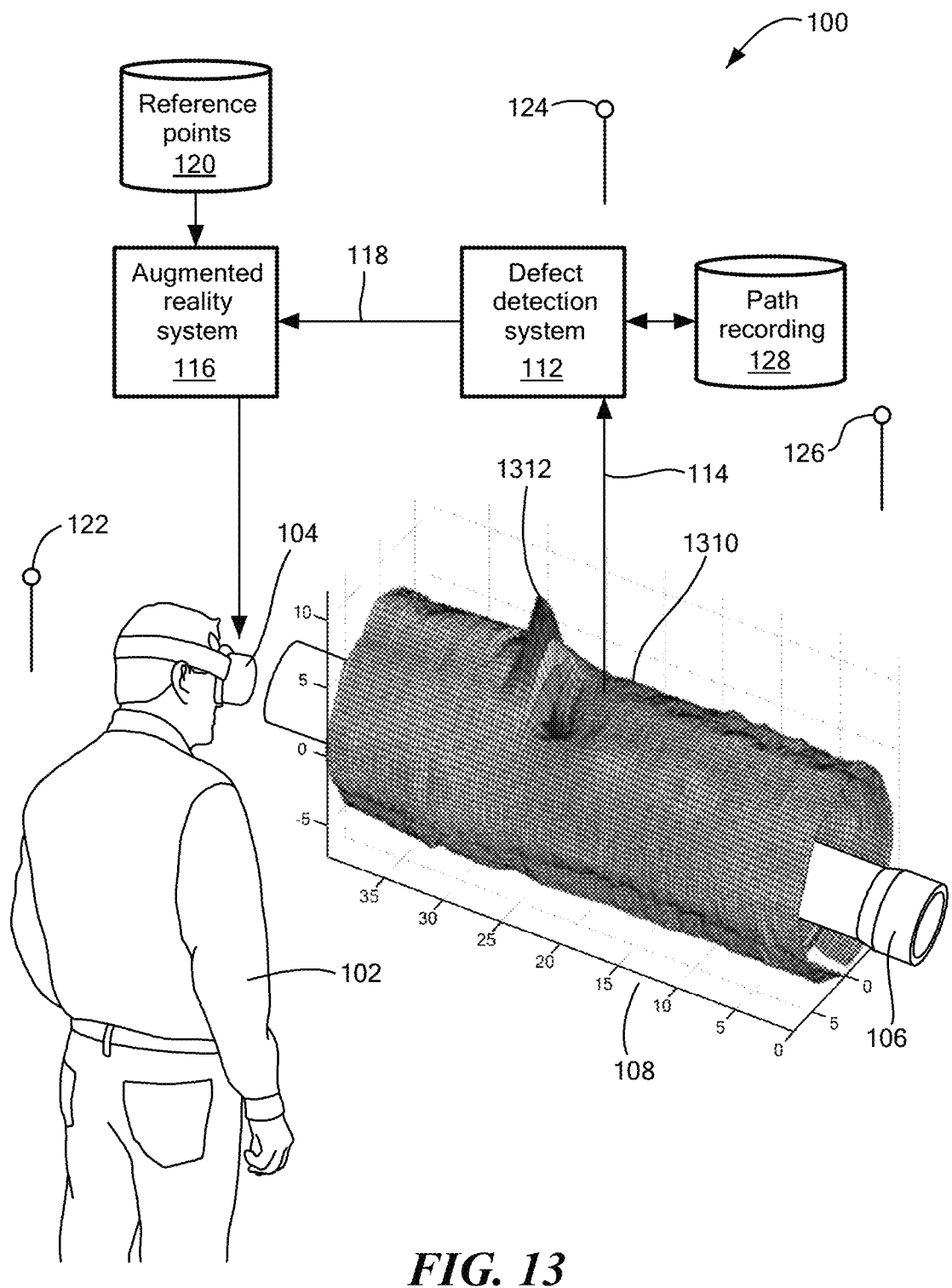
FIG. 13 is a schematic diagram of the system of FIG. 1, including an illustration of a hypothetical augmented reality scene, as augmented by the system to display a surface plot of relative magnetic field strength along the pipe, according to another embodiment of the present invention.

FIG. 13 illustrates yet another type of image 108 the system 100 may generate to represent the magnetic field data. In this embodiment, the magnetic field data are represented by a surface plot 1310 of relative magnetic field strength, after residual magnetic fields, such as from welds, have been automatically removed by the defect detection system 112, as discussed in the '471 and '472 patents. A defect is indicated by a characteristic shape 1312 in the surface plot 1310. Optionally, the surface plot 1310 may be partially transparent (not shown), so the pipe 106 may be more clearly seen.

Figure 14:
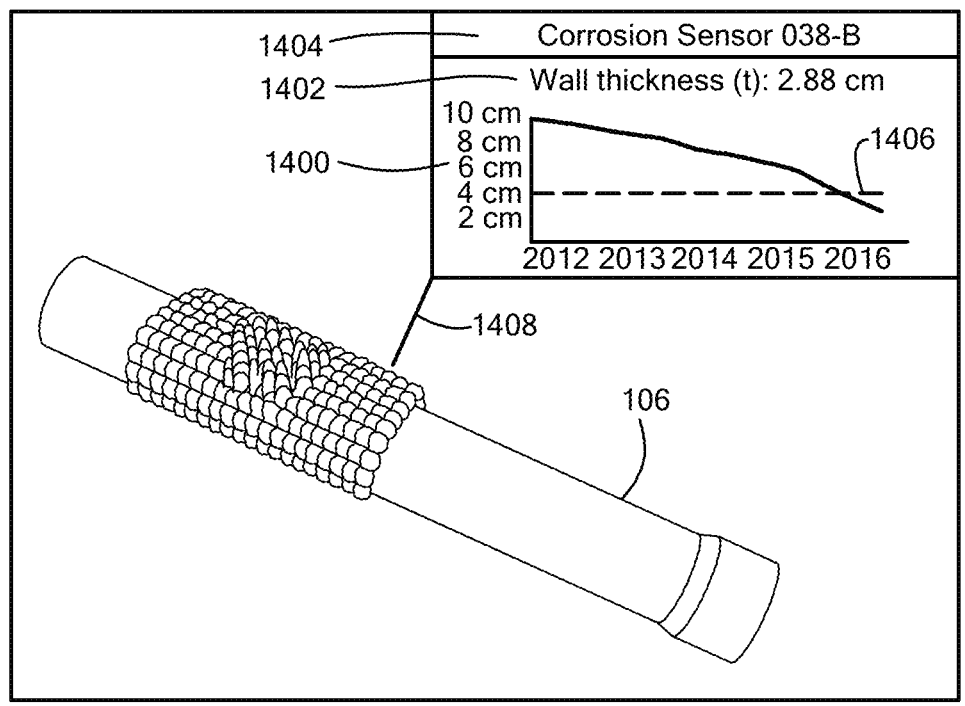
FIGS. 14 and 15 illustrate hypothetical augmented reality scenes, as augmented by the system of FIG. 1 to display historical information about detected defects, according to an embodiment of the present invention.
Figure 15:
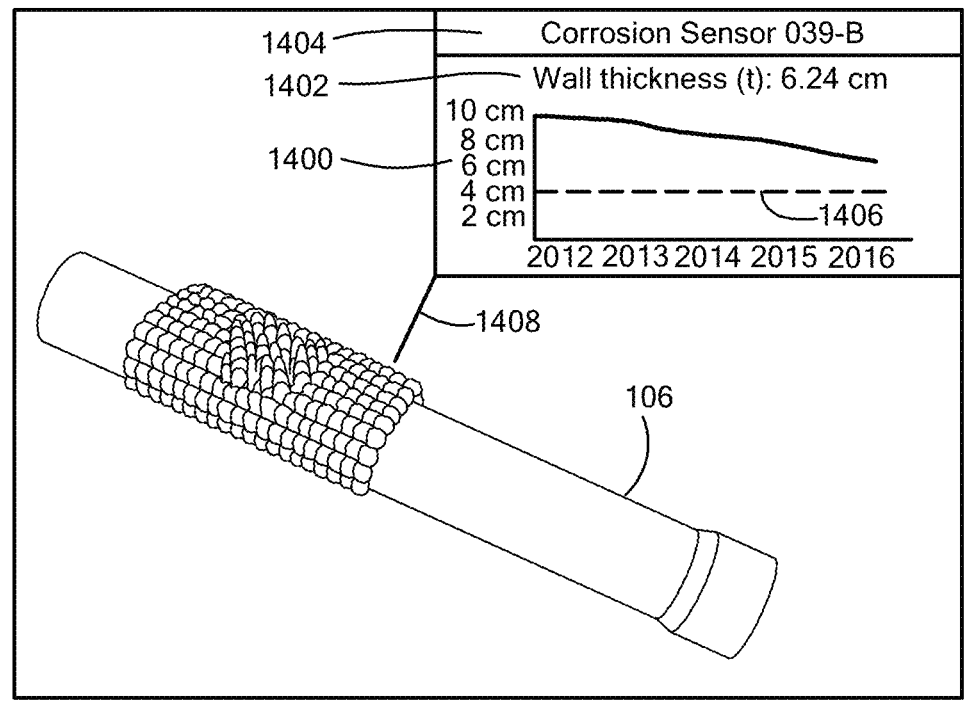

FIGS. 14 and 15 illustrate hypothetical augmented reality scenes, as augmented by the system of FIG. 1 to display historical information about detected defects or a condition of the ferromagnetic material in general. In FIGS. 14 and 15, the augmented reality system 116 causes the display device 104, 1002 or 1102 to display a graph 1400 of pipe wall thickness over time, as well as the current wall thickness 1402, as estimated by the defect detection system 112. The display includes information 1404 identifying the magnetometer proximate the location on the pipe 106 where the wall thickness estimates have been calculated. The graph 1400 may include a dashed line 1406 indicating a predetermined value, such as a value below which the wall thickness warrants repair. Wall thicknesses less this predetermined value may trigger the system 100 to highlight corresponding portions of the magnetic field data. For example, the system 100 may color corresponding portions of the defect depth plot 110 (FIG. 1) different, such as red, from other portions of the plot 110.

Returning to FIGS. 14 and 15, the background of the information 1404 identifying the magnetometer may be color coded. For example, if the current estimated wall thickness is less than the predetermined value 1406, as in FIG. 14, the background may be red, whereas if the current estimated wall thickness is greater than the predetermined value 1406, as in FIG. 15, the background may be black. The display may include a line 1408 extending from the graph 1400 to the icon representing the magnetometer identified in the information 1404.

Figure 16:
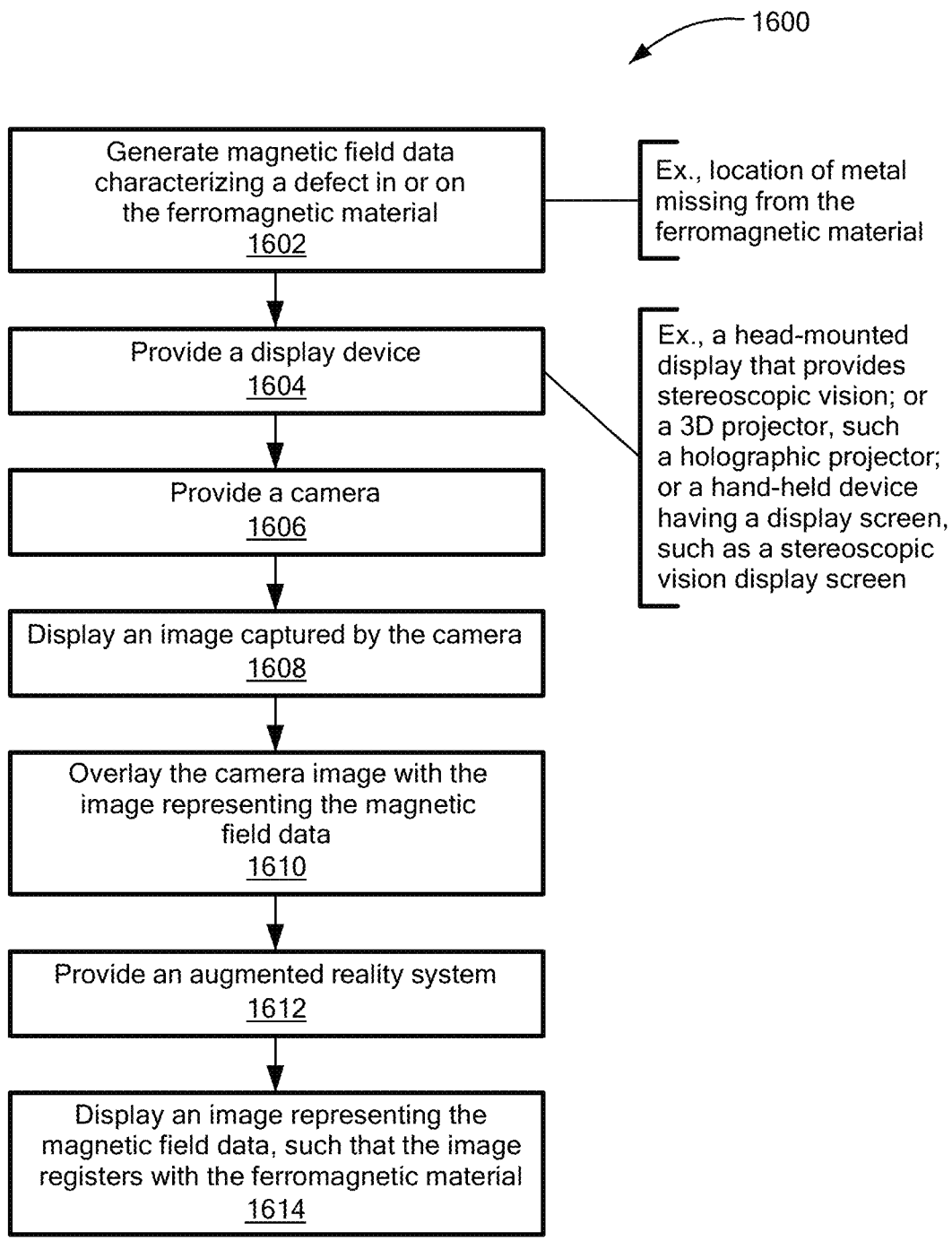
FIGS. 16-18 provide flowcharts schematically illustrating a method for visualizing defects in ferromagnetic material, and operations performed by a system for visualizing defects in ferromagnetic material, according to embodiments of the present invention.
Figure 17:
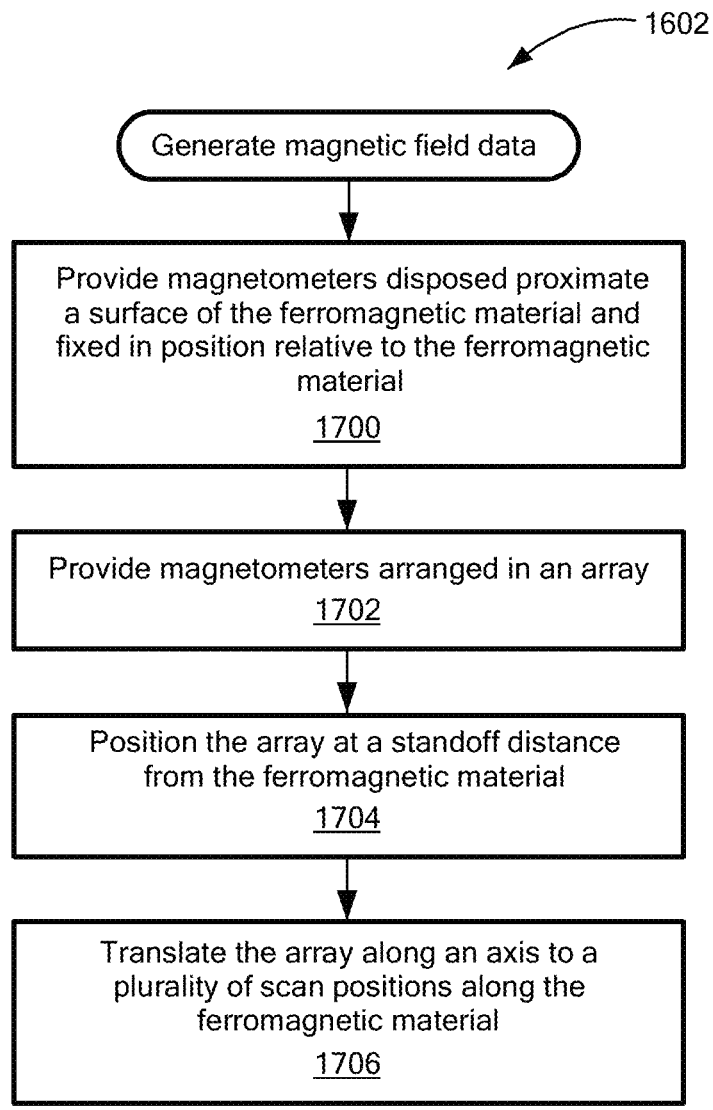
Figure 18:
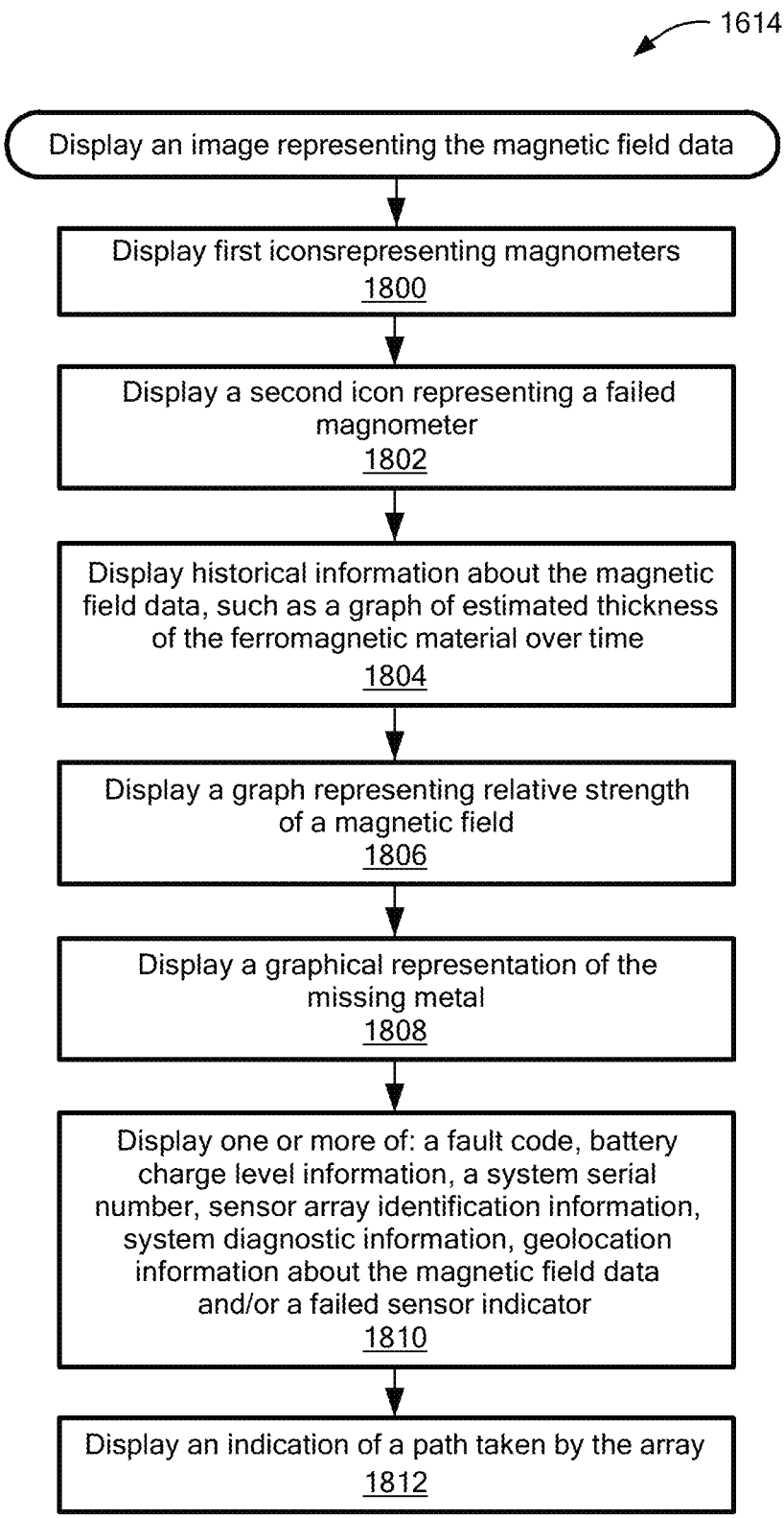

FIGS. 16-18 provide flowcharts schematically illustrating a method 1600 for visualizing defects in ferromagnetic material, and operations performed by a system for visualizing defects in ferromagnetic material. At 1602, magnetic field data characterizing location of the defect on or in a ferromagnetic material is generated. The defect may be metal missing from the ferromagnetic material. FIG. 17 contains a flowchart of operations that may be performed to generate the magnetic field data. For example, in some embodiments, at 1700, magnetometers are provided. The magnetometers are disposed proximate a surface of the ferromagnetic material and fixed in position, relative to the ferromagnetic material. In some embodiments, at 1702, magnetometers that are arranged in an array are provided. At 1704, the array is positioned at a standoff distance from the ferromagnetic material. At 1706, the array is translated along an axis to a plurality of scan positions along the ferromagnetic material.

Returning to FIG. 16, at 1604, a display device is provided. The display device may include a head-mounted display that provides stereoscopic vision. The display device may include a 3D projector, such as a holographic projector. The display device may include a hand-held device having a display screen. The display screen may include a stereoscopic vision display screen.

Optionally, at 1606, a camera is provided. Optionally, at 1608, the camera captures an image of the real world. Optionally, at 1610, the camera image of the real world is overlaid with the image representing the magnetic field data.

At 1612, an augmented reality system is provided. At 1614, the augmented reality system causes the display device to display an image representing the magnetic field data, such that the image registers with the ferromagnetic material. FIG. 18 contains a flowchart of operations that may be performed to display the image. For example, in some embodiments, at 1800, a first icon representing a plurality of magnetometers is displayed. In some embodiments, at 1802, a second icon, visually distinct from the first icon, is displayed to represent a failed magnetometer.

In some embodiments, at 1804, historical information about the magnetic field data is displayed. For example, a graph of estimated thickness of the ferromagnetic material over time may be displayed. In some embodiments, at 1806, a graph representing relative strength of a magnetic field is displayed. In some embodiments, at 1808, a graphical representation of missing metal or defect is displayed. In some embodiments, at 1810, one or more of the following is displayed: a fault code, battery charge level information, a system serial number, sensor array identification information, system diagnostic information, geolocation information about the magnetic field data and/or a failed sensor indicator. The geolocation information may include, for example, latitude and longitude (or other coordinates) of a defect, magnetometer, magnetometer array or section of pipe hosing a defect. In some embodiments, at 1812, an indication of a path taken by the array of magnetometers is displayed.

Thus, embodiments of the present invention may use augmented reality technology to virtually overlay onto a physical scene a depth contour map, or other information, that the magnetometer array has observed. The magnetometry data from the array may be loaded into the augmented reality system, and the augmented reality system, based on previous tagging of local landmarks to provide a spatial reference frame, can overlay in 3D this defect map onto the array, or the insulation, or the pipe coating, or the pipe itself (as layers are removed), and then be used to visually guide a validating independent inspection process. Furthermore, this visual reference process can be used to accurately place the sensor array back in its original location, even though all references on the insulation may have been lost when the insulation was removed or destroyed. This return-to-original-location is useful to enable continued observation of changes in the pipe area that is under the sensor array, relative to historical data previously collected.

The system includes augmented reality display hardware, which may include a projector, and an augmented reality visualization system coupled to the augmented reality display hardware. The augmented reality visualization system is also coupled to the defect detection system. The ARV system is configured to display to a user, via the display hardware, an image of, or other information about, a defect that corresponds to a plurality of data points identified by the defect detection system. The image is displayed so as to coincide with a location proximate the surface of the ferromagnetic material where the data points were identified. That is, when a user gazes at the location on the ferromagnetic material output by the defect detection system, the augmented reality visualization system generates the image of the defect or other information, so the user visualizes the defect or other information on or in the ferromagnetic material. In some embodiments, when a user gazes at the location on the ferromagnetic material output by the defect detection system, the augmented reality visualization system generates the image of the defect, so the image is superimposed on the user's view of the actual ferromagnetic material, and the image of the defect registers on the location of the defect in the ferromagnetic material.

While the invention is described through the above-described exemplary embodiments, modifications to, and variations of, the illustrated embodiments may be made without departing from the inventive concepts disclosed herein. For example, although specific parameter values, such as dimensions and materials, may be recited in relation to disclosed embodiments, within the scope of the invention, the values of all parameters may vary over wide ranges to suit different applications. Unless otherwise indicated in context, or would be understood by one of ordinary skill in the art, terms such as "about" mean within ±20%.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module" are for convenience and not intended to limit its implementation. All or a portion of each block, module or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The defect detection system and/or the augmented reality visualization system, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

What is claimed is:

1. A system for visualizing defects in ferromagnetic material, the system comprising:
    a source of magnetic field data, the magnetic field data characterizing location of a defect in the ferromagnetic material;
    a display device configured to generate an image perceivable by a human; and
    an augmented reality system coupled to receive the magnetic field data and cause display, by the display device, of an image representing the magnetic field data, such that the image registers, as viewed by the human, with the ferromagnetic material, wherein the image comprises a two-dimensional and/or three-dimensional array of the magnetic field data, and the display device is configured to align the two-dimensional and/or three-dimensional array with surface contours of the ferromagnetic material.

2. A system according to claim 1, wherein the magnetic field data characterizes location of metal missing from the ferromagnetic material.

3. A system according to claim 1, wherein the display device comprises a head-mounted display.

4. A system according to claim 3, wherein the display device comprises a stereoscopic vision display device.

5. A system according to claim 1, wherein the display device comprises a 3D projector.

6. A system according to claim 5, wherein the display device comprises a holographic projector.

7. A system according to claim 1, wherein the display device comprises a hand-held device comprising a display screen.

8. A system according to claim 7, wherein the display screen comprises a stereoscopic vision display screen.

9. A system according to claim 1, wherein the display device further comprises a camera, and the display device is configured to display an image captured by the camera, overlaid with the image representing the magnetic field data.

10. A system according to claim 1, wherein the image representing the magnetic field data comprises first icons representing magnetometers that detected a magnetic field proximate the ferromagnetic material and from which the magnetic field data was derived, such that the first icons register, as viewed by the human, with the ferromagnetic material.

11. A system according to claim 10, wherein the image representing the magnetic field data comprises a second icon, visually distinct from the first icons, representing a failed magnetometer.

12. A system according to claim 1, wherein the image representing the magnetic field data comprises historical information about the magnetic field data.

13. A system according to claim 12, wherein the historical information comprises a graph showing estimated thickness of the ferromagnetic material over time.

14. A system according to claim 1, wherein the image representing the magnetic field data comprises a graph representing relative strength of a magnetic field proximate the ferromagnetic material and from which the magnetic field data was derived, such that the graph registers, as viewed by the human, with the ferromagnetic material.

15. A system according to claim 1, wherein the image representing the magnetic field data comprises a graphical representation of the defect in the ferromagnetic material, such that the graphical representation registers, as viewed by the human, with the ferromagnetic material.

16. A system according to claim 1, wherein the image representing the magnetic field data comprises a defect depth map, such that the defect depth map registers, as viewed by the human, with the ferromagnetic material.

17. A system according to claim 1, wherein the image representing the magnetic field data comprises one or more of: a fault code, battery charge level information, a system serial number, sensor array identification information, system diagnostic information, geolocation information about the magnetic field data represented in the image and/or a failed sensor indicator.

18. A system according to claim 1, wherein the source of magnetic field data comprises a plurality of magnetometers disposed proximate a surface of the ferromagnetic material, wherein each magnetometer of the plurality of magnetometers is fixed in position, relative to the ferromagnetic material.

19. A system according to claim 1, wherein the source of magnetic field data comprises a plurality of magnetometers arranged in an array, the array being positionable at a standoff distance from the ferromagnetic material and translatable along an axis to a plurality of scan positions along the ferromagnetic material.

20. A system according to claim 19, wherein the image representing the magnetic field data comprises an indication of a path taken by the array, such that the indication of the path registers, as viewed by the human, with the ferromagnetic material.

21. A method for visualizing defects in ferromagnetic material, the method comprising:
    generating magnetic field data, the magnetic field data characterizing location of a defect in the ferromagnetic material;
    providing a display device configured to generate an image perceivable by a human;
    providing an augmented reality system coupled to receive the magnetic field data; and
    displaying, by the display device, an image representing the magnetic field data, such that the image registers, as viewed by the human, with the ferromagnetic material, wherein the image comprises a two-dimensional and/or three-dimensional array of the magnetic field data, and the display device is configured to align the two-dimensional and/or three-dimensional array with surface contours of the ferromagnetic material.

22. A method according to claim 21, wherein the magnetic field data characterizes location of metal missing from the ferromagnetic material.

23. A method according to claim 21, wherein providing the display device comprises providing a head-mounted display.

24. A method according to claim 23, wherein providing the display device comprises providing a stereoscopic vision display device.

25. A method according to claim 21, wherein providing the display device comprises providing a 3D projector.

26. A method according to claim 25, wherein providing the display device comprises providing a holographic projector.

27. A method according to claim 21, wherein providing the display device comprises providing a hand-held device comprising a display screen.

28. A method according to claim 27, wherein providing the display screen comprises providing a stereoscopic vision display screen.

29. A method according to claim 21, further comprising:
providing a camera;
displaying, by the display device, an image captured by the camera; and
overlaying the image captured by the camera with the image representing the magnetic field data.

30. A method according to claim 21, wherein displaying the image representing the magnetic field data comprises displaying first icons representing magnetometers that detected a magnetic field proximate the ferromagnetic material and from which the magnetic field data was derived, such that the first icons register, as viewed by the human, with the ferromagnetic material.

31. A method according to claim 30, wherein displaying the image representing the magnetic field data comprises displaying a second icon, visually distinct from the first icons, representing a failed magnetometer.

32. A method according to claim 21, wherein displaying the image representing the magnetic field data comprises displaying historical information about the magnetic field data.

33. A method according to claim 32, wherein displaying the historical information comprises displaying a graph showing estimated thickness of the ferromagnetic material over time.

34. A method according to claim 21, wherein displaying the image representing the magnetic field data comprises displaying a graph representing relative strength of a magnetic field proximate the ferromagnetic material and from which the magnetic field data was derived, such that the graph registers, as viewed by the human, with the ferromagnetic material.

35. A method according to claim 21, wherein displaying the image representing the magnetic field data comprises displaying a graphical representation of the defect in the ferromagnetic material, such that the graphical representation registers, as viewed by the human, with the ferromagnetic material.

36. A method according to claim 21, wherein displaying the image representing the magnetic field data comprises displaying a defect depth map, such that the defect depth map registers, as viewed by the human, with the ferromagnetic material.

37. A method according to claim 21, wherein displaying the image representing the magnetic field data comprises displaying one or more of: a fault code, battery charge level information, system serial number, sensor array identification information, system diagnostic information, geolocation information about the magnetic field data represented in the image and/or a failed sensor indicator.

38. A method according to claim 21, wherein generating the magnetic field data comprises providing a plurality of magnetometers disposed proximate a surface of the ferromagnetic material, wherein each magnetometer of the plurality of magnetometers is fixed in position, relative to the ferromagnetic material.

39. A method according to claim 21, wherein generating the magnetic field data comprises:
providing a plurality of magnetometers arranged in an array;
positioning the array at a standoff distance from the ferromagnetic material; and
translating the array along an axis to a plurality of scan positions along the ferromagnetic material.

40. A method according to claim 39, wherein displaying the image representing the magnetic field data comprises displaying an indication of a path taken by the array, such that the indication of the path registers, as viewed by the human, with the ferromagnetic material.

41. A computer program product for visualizing defects in ferromagnetic material, the computer program product comprising a non-transitory computer-readable medium having computer readable program code stored thereon that, when executed by a processor, establishes processes, the processes comprising:
a process that generates magnetic field data, the magnetic field data characterizing location of a defect in the ferromagnetic material;
a process driving a display device configured to generate an image perceivable by a human; and
an augmented reality process coupled to receive the magnetic field data and cause display, by the display device, of an image representing the magnetic field data, such that the image registers, as viewed by the human, with the ferromagnetic material, wherein the image comprises a two-dimensional and/or three-dimensional array of the magnetic field data, and the display device is configured to align the two-dimensional and/or three-dimensional array with surface contours of the ferromagnetic material.

42. A computer program product according to claim 41, wherein the magnetic field data characterizes location of metal missing from the ferromagnetic material.

* * * * *